United States Patent [19]

Graf et al.

[11] Patent Number: 4,851,584

[45] Date of Patent: Jul. 25, 1989

[54] PREPARATION OF CARBONYL COMPOUNDS

[75] Inventors: Fritz Graf, Speyer; Leopold Hupfer, Friedelsheim; Harald Schultheiss, Frankenthal, all of Fed. Rep. of Germany

[73] Assignee: BASF Aktiengesellschaft, Ludwigshafen, Fed. Rep. of Germany

[21] Appl. No.: 176,106

[22] Filed: Mar. 30, 1988

[30] Foreign Application Priority Data

Apr. 15, 1987 [DE] Fed. Rep. of Germany ....... 3712856

[51] Int. Cl.[4] ............................................. C07C 45/38
[52] U.S. Cl. ..................................... 568/471; 568/473
[58] Field of Search ................ 568/473, 471, 480, 486

[56] References Cited

U.S. PATENT DOCUMENTS

| 4,282,374 | 8/1981 | Engelbach et al. | 568/471 |
| 4,503,261 | 3/1985 | Sauer et al. | 568/471 |

FOREIGN PATENT DOCUMENTS

| 0007570 | 1/1984 | European Pat. Off. | 568/471 |
| 2158343 | 5/1972 | Fed. Rep. of Germany | 568/471 |
| 1967147 | 6/1979 | Fed. Rep. of Germany | 568/471 |
| 1923048 | 7/1979 | Fed. Rep. of Germany | 568/471 |
| 1272592 | 5/1972 | United Kingdom | 568/471 |
| 1361190 | 7/1974 | United Kingdom | 568/471 |

*Primary Examiner*—Werren B. Lone
*Attorney, Agent, or Firm*—John H. Shurtleff

[57] ABSTRACT

A process for the preparation of carbonyl compounds by oxidation of alcohols in the gas phase with a gas containing oxygen in the presence of catalysts containing copper and silver.

9 Claims, No Drawings

PREPARATION OF CARBONYL COMPOUNDS

The present invention relates to a novel process for the preparation of carbonyl compounds by oxidation of alcohols in the gas phase by means of a gas containing oxygen in the presence of catalysts containing copper and silver.

It is known from German Pat. Nos. 19 23 048 and 19 67 147 that glyoxal can be prepared from ethylene glycol by oxidation in the gas phase over an oxidation catalyst containing copper in combination with tin, phosphorus, arsenic, antimony, or bismuth or silver in combination with phosphorus. However, in these processes high yields of glyoxal are achieved only at the expense of incomplete conversion, i.e. the residual glycol contents are high. Furthermore, the yields decline after prolonged production, which necessitates regeneration of the catalysts by expensive methods (cf. German Laid-Open Application No. 21 58 343).

In the process disclosed in European Pat. No. 7 570 oxidation of ethylene glycol in the gas phase over copper catalysts is carried out in the presence of a volatile phosphorus compound, and good results and obtained with respect to catalyst life and glyoxal yield. It has been found after prolonged operation however that the glyoxal yield and the purity of the product deteriorate progressively with duration of production.

The use of catalyst beds consisting of copper and silver crystals also gives a product whose quality is unsatifactory, in particular because of the high residual glycolaldehyde content. In this process (U.S. Pat. No. 4,503,261) the ethylene glycol is oxidized at high temperatures (from 450° C. to 800° C.) and the residence time is short (not more than 0.05 s).

The presence of glycol and side products such as glycolaldehyde and formaldehyde in glyoxal is highly undesirable for many applications. Since it is not possible to remove glycol and glycolaldehyde from glyoxal at a reasonable cost it was necessary to seek a process that would allow preparation of glyoxal by catalytic oxidation of ethylene glycol in the gas phase largely without the formation of troublesome side products, even after long periods of operation.

We have now found that the preparation of carbonyl compounds of the formula I—where $R^1$ is a hydrogen atom and $R^2$ is the group $OR^5$ or $R^1$ and $R^2$ together are an oxygen atom, $R^3$ is a hydrogen atom, alkyl of from 1 to 8 carbon atoms, or cycloalkyl, $R^4$ is a hydrogen atom or alkyl of from 1 to 3 carbon atoms, and $R^5$ is alkyl of from 1 to 4 carbon atoms, cycloalkyl, or alkoxyalkyl (which may include a keto or aldehyde group)

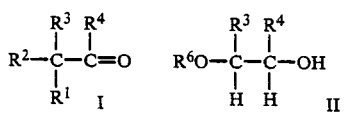

from alcohols of the formula II—where $R^3$ and $R^4$ are as given above and $R^6$ is a hydrogen atom, alkyl or hydroxyalkyl of from 1 to 4 carbon atoms, cycloalkyl, or alkoxyalkyl (which may carry a hydroxyl group)—by oxidation in the gas phase with a gas containing oxygen, in the presence of catalysts containing copper and silver, can be performed particularly advantageously if the gaseous starting mixture is led first over a copper catalyst whose active part contains more than 90% copper by weight, then over a silver catalyst whose active part contains more than 90% silver by weight, at temperatures of from 200° C. to 450° C.

By the novel process glyoxal, for instance, is obtained from ethylene glycol in high yield and purity, even in sustained production.

In the alcohols of formula II, alkyl means methyl, ethyl, propyl, or butyl for instance, and cycloalkyl means radicals such as cyclohexyl and cyclopentyl. Alkoxyalkyl that may carry a hydroxyl group includes HO $CH_2CH_2$ O $CH_2CH_2$—for example. In the novel process aldehyde groups are formed at the sites of terminal hydroxyl groups, keto groups are formed at the sites of secondary hydroxyl groups.

The following are examples of starting compounds of formula II:

$HOCH_2CH_2OH$, $CH_3OCH_2CH_2OH$, $C_2H_5OCH_2CH_2OH$ $CH_3CH(OH)CH_2OH$, $C_2H_5CH(OH)CH_2OH$,

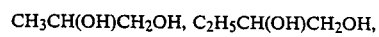—$CH(OH)CH_2OH$, $HOCH_2CH_2OCH_2CH_2OH$,

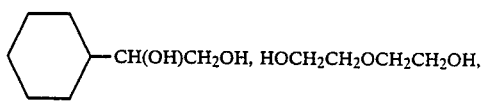

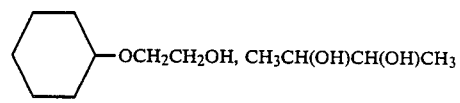—$OCH_2CH_2OH$, $CH_3CH(OH)CH(OH)CH_3$

Oxidation of the alcohol in the gas phase with the gas containing oxygen is carried out at temperatures of from 200° to 450° C., preferably at from 300° C. to 400° C.

The catalysts are metallic copper and silver or alloys in which the mass fraction of copper or silver is more than 90%. They are employed in the form of turnings, wire mesh, or gauze, or they may be applied to supports, for example inert materials of low specific surface. It is expedient to employ shell-type catalysts, which consist of inert cores coated with the active material (one of the metals described above). These catalysts are simple to prepare by coating an inert material such as alpha-alumina, silicon carbide, or steatite with the metal by known methods, such as flame coating, plasma coating, or sputtering. Particularly suitable shell-type catalysts can be made from steatite for instance, which can be in forms such as spherules, rings, or half-rings and is coated with copper or silver whose mass is typically from 0.1% to 10% of the mass of the finished catalyst.

Surprisingly, the advantageous results of the novel process are achieved just through the use of a combination of massive, pure copper, to which nothing is added, and a silver shell-type catalyst of the kind described.

In an advantageous embodiment of the invention oxidation in the gas phase is carried out in the presence of a phosphorus compound that is volatile under the conditions of the reaction.

It is expedient to use phosphorus compounds that vaporize without decomposition and do not react with components of the synthesis gas under the conditions of the process as the phosporus compound that is volatile under the conditions of the reaction. These include, for instance, esters of phosphoric acid, phosphorous acid, or phosphonic acids, such as trimethyl phosphate, triethyl phosphate, triisopropyl phosphate, tripropyl phosphate, trimethyl phosphite, triethyl phosphite, triethylphosphine oxide, diethyl methylphosphonate, dimethyl methylphosphonate, and diethyl ethylphosphonate. The amounts of the phosphorus compounds employed are such that the ratio of the mass of phosphorus to the mass of the alcohol is from 0.01 ppm to 10 ppm.

The process can be carried out in the following way, for example: a gaseous mixture of oxygen and the alcohol in the proportion of between about 0.5 mol and 2 mol oxygen to 1 mol alcohol, possibly diluted with nitrogen (up to 99% of the volume of the complete gas mixture), is led over the catalysts, which are maintained at a temperature of from 225° C. to 500° C., after introduction of any volatile phosphorus compound that is to be employed into the initial gaseous mixture. The residence time of the reaction mixture in the reactor is from 0.5 s to 3 s. The gases pass over the copper catalyst first, then over the silver catalyst; the part of the catalyst bed nearest the inlet of the reactor consists of copper catalyst, and the remainder consists of silver catalyst.

The gaseous reaction mixture is scrubbed with water when it leaves the reactor, as usual.

In order to obtain better control of the amount of phosphorus to be added at trace levels it may be expedient to dissolve the phosphorus compound in water or the alcohol and meter the solution into the stream of hot synthesis gas.

The glyoxal prepared by the novel process from ethylene glycol can be obtained directly in a commercial form, i.e. as a 40% aqueous solution.

The novel process provides carbonyl compounds, especially the aldehydes glyoxal and methylglyoxal, of excellent purity and in quite good yields. It is surprising that, for instance, glyoxal of such outstanding quality should be obtained at the comparatively low temperature of about 360° C. and by the use of pure copper and silver. The introduction of volatile phosphorus compounds reduces the residual glycolaldehyde content but does not increase the yield.

EXAMPLE 1

A tube reactor 50 cm long and of internal diameter 20 mm was packed with 33 ml of catalyst consisting of copper turnings made from phosphorus-free copper of more than 99.9% purity. Over the copper 67 ml of silver shell-type catalyst, prepared as described below, was introduced into the reactor. The bed of copper catalyst was nearer to the reactor inlet.

A mixture of 12.4 g of ethylene glycol, 27 liters (at s.t.p) of air, and 100 liters (at s.t.p.) of nitrogen was passed each hour through the reactor, which was maintained at a temperature of 360° C. by means of a bath of molten salt.

The reaction gas leaving the reactor was brought into contact with water, which dissolved the products of the reaction, apart from the permanent gases carbon monoxide and carbon dioxide, which remained in the exhaust gases and were determined analytically in the gas phase. The glycol conversion was 99%.

The yield of glyoxal was 71.5% that of glycolaldehyde only 0.3%. Conversion to formaldehyde and acids was 0.8% and 2.0% respectively. Combustion to carbon monoxide and dioxide amounted to 24.4%. These results correspond to mass fractions of 0.6% glycol and 0.2% glycolaldehyde in the commercial 40% aqueous solution of glyoxal; the corresponding formaldehyde fraction is 0.46%.

The silver shell-type catalyst was prepared as follows. In an open revolving drum 0.5 liter of steatite spherules of diameter from 3.5 mm to 4.5 mm were flame-coated with silver powder of particle size less than 0.06 mm, the powder being introduced into an oxyacetylene flame and carried, partly molten, onto the support. The weight of silver was such that the mass fraction of silver contained by the finished catalyst was 4%. The temperature of the material to be coated was from 400° C. to 600° C. The coating process lasted 20 min.

EXAMPLE 2

(Comparison—only silver)

The tube reactor described in Example 1 was packed with 100 ml of the silver shell-type catalyst as used in Example 1. A mixture of 6.2 g of ethylene glycol, 13.5 liters (at s.t.p.) of air and 100 liters (at s.t.p.) of nitrogen was passed each hour through the reactor, which was maintained at a temperature of 360° C. by means of a bath of molten salt. The product was separated and the gases were analysed as described in Example 1.

The glycol conversion was 97.4%. The yield of glyoxal was 70.6%. Combustion to carbon monoxide and dioxide amounted to 22.9%. Conversion to glycolaldehyde, formaldehyde, and acids was 1.4%, 0.9%, and 1.6% respectively. These results correspond to mass fractions of 1.6% glycol and 0.9% glycolaldehyde in the commercial 40% solution of glyoxal, the corresponding formaldehyde fraction is 0.53%.

EXAMPLE 3

(Comparison—only copper)

A tube reactor of internal diameter 20 mm packed with 100 ml of massive phosphorus-free copper in the form of Raschig rings measuring 5 mm×5 mm×0.3 mm. A mixture of 12.4 g of ethylene glycol, 27 liters (at s.t.p.) of air, and 100 liters (at s.t.p.) of nitrogen was passed each hour through the reactor, which was maintained at a temperature of 350° C. by means of a bath of molten salt. The product was separated and the gases were analysed as described in Example 1.

The yield of glyoxal was 49.7%, the glycol conversion was 89.8%. Combustion to carbon monoxide and dioxide amounted to 29.1%. Conversion to glycolaldehyde, formaldehyde, and acids was 1.0%, 8.0%, and 2.0% respectively. These results correspond to mass fractions of 9.0% glycol and 0.9% glycolaldehyde in the commercial 40% solution of glyoxal; the corresponding formaldehyde fraction is 6.9%.

EXAMPLE 4

The catalysts and reaction conditions were the same as in Example 1 but sufficient trimethyl phosphate was introduced to make the ratio of the mass of phosphorus to the mass of ethylene glycol equal to 0.33 ppm.

The yield of glyoxal was 71.2%, the glycol conversion was 98.7%. Combustion to carbon monoxide and dioxide amounted to 24.6%. Conversion to glycolaldehyde, formaldehyde, and acids was 0.2%, 0.9%, and 1.8% respectively. These results correspond to mass fractions of 0.8% glycol and 0.1% glycolaldehyde in the commercial 40% solution of glyoxal; the corresponding formaldehyde fraction is 0.53%.

We claim:
1. In a process for the preparation of carbonyl compounds of the formula

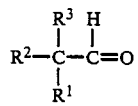

where $R^1$ is a hydrogen atom and $R^2$ is the group $OR^4$ or $R^1$ and $R^2$ together are an oxygen atom, $R^3$ is a hydrogen atom or alkyl of from 1 to 8 carbon atoms, and $R^4$ is alkyl of from 1 to 4 carbon atoms, from alcohols of the formula

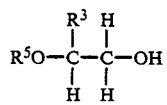

where $R^3$ is given above and $R^5$ is a hydrogen atom or alkyl of from 1 to 4 carbon atoms, by oxidation in the gas phase with a gas containing oxygen in the presence of catalysts containing copper and silver, the improvement which comprises:

leading the gaseous starting mixture in a reactor first over a copper catalyst whose active part contains at least 90% copper by weight, and then over a silver catalyst whose active part contains at least 90% silver by weight, at temperatures of from 200° C. to 450° C., and at a residence time of the reaction mixture in the reactor of from 0.5 to 3 seconds.

2. A process as claimed in claim 1 wherein glyoxal is prepared from ethylene glycol.

3. A process as claimed in claim 1 wherein the oxidation in the gas phase is carried out in the presence of a phosphorus compound that is volatile under the conditions of the reaction, the ratio of the mass of phosphorus to the mass of the alcohol being from 0.01 ppm to 10 ppm.

4. A process as claimed in claim 1 wherein copper particles in which the mass fraction of copper is at least 90% are used as the copper catalyst.

5. A process as claimed in claim 1 wherein the copper catalyst is a shell-type catalyst consisting of an inert support and a coating of active material thereon that contains more than 90% copper by weight.

6. A process as claimed in claim 1 wherein the silver catalyst is a shell-type catalyst consisting of an inert support and a coating of active material thereon that contains more than 90% silver by weight.

7. A process as claimed in claim 1 wherein the alcohol of the formula II is one of the compounds having the formula:

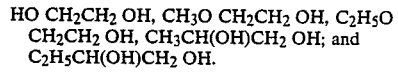

8. A process as claimed in claim 1 in which the reaction temperature is from 300°C. to 400° C.

9. A process as claimed in claim 8 wherein glyoxal is prepared from ethylene glycol.

* * * * *